United States Patent [19]

Langberg

[11] Patent Number: 4,945,912

[45] Date of Patent: Aug. 7, 1990

[54] CATHETER WITH RADIOFREQUENCY HEATING APPLICATOR

[75] Inventor: Edwin Langberg, Medford, N.J.

[73] Assignee: Sensor Electronics, Inc., Mt. Laurel, N.J.

[21] Appl. No.: 276,294

[22] Filed: Nov. 25, 1988

[51] Int. Cl.⁵ .......................... A61B 5/04; A61N 5/00
[52] U.S. Cl. ..................... 128/642; 128/401; 128/786; 128/804; 606/33
[58] Field of Search .............. 128/784, 786, 804, 401, 128/303.13, 642, 303.1; 600/12; 606/33

[56] References Cited

U.S. PATENT DOCUMENTS

| | | | |
|---|---|---|---|
| 4,154,246 | 5/1979 | LeVeen | 128/784 |
| 4,583,556 | 4/1986 | Hines et al. | 128/784 |
| 4,641,649 | 2/1987 | Walinsky et al. | 128/303.1 |
| 4,700,716 | 10/1987 | Kasevich et al. | 128/804 |
| 4,785,815 | 11/1988 | Cohen | 128/642 |
| 4,825,880 | 5/1989 | Stauffer et al. | 128/804 |

FOREIGN PATENT DOCUMENTS

| | | | |
|---|---|---|---|
| 0249631 | 9/1987 | German Democratic Rep. | 128/642 |
| 1266548 | 10/1986 | U.S.S.R. | 128/804 |

OTHER PUBLICATIONS

Ryan et al., "Variations in the Design . . . Hyperthemia", Proc. 14th Annual NF Bio Conf. IEEE, Mar. 1988, pp. 130–132.

Satoh et al., "Implantable helical coil microwave antenna . . . ", Int. J. Hypertheromia, vol. 4, No. 5, 1988, pp. 497–512.

Lyons et al., "Localized Hyperthermia . . . Array", IEEE Trans. Biomed Eng., vol. 31, No. 1, pp. 53–54, Jan. 1984.

Lin et al., "An implantable . . . Hyperthermia", Proc. of the IEEE, vol. 75, No. 8, pp. 1132–1133, Aug. 1987.

Primary Examiner—Lee S. Cohen

[57] ABSTRACT

Radiofrequency (RF) heating applicator, located at the distal end of a coaxial line catheter, produces deeper and more uniform heat dissipation. The active applicator element is a conductor helix fed via the coaxial line. The applicator has provisions for interception of intracardiac electrogram signal. A cardiac ablation system using the above catheter, ablates cardiac tissue responsible for ventricular tachycardia. The ablation system provides means to monitor intracardiac electrograms and to control the RF power. A variation of the helical applicator can be used in a hyperthermia system for treatment of malignant tumors.

10 Claims, 2 Drawing Sheets

U.S. Patent   Aug. 7, 1990   Sheet 1 of 2   4,945,912
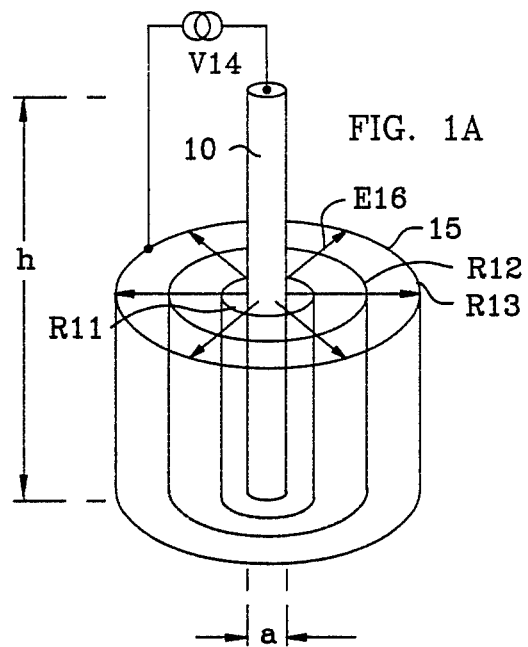
FIG. 1A
FIG. 1B
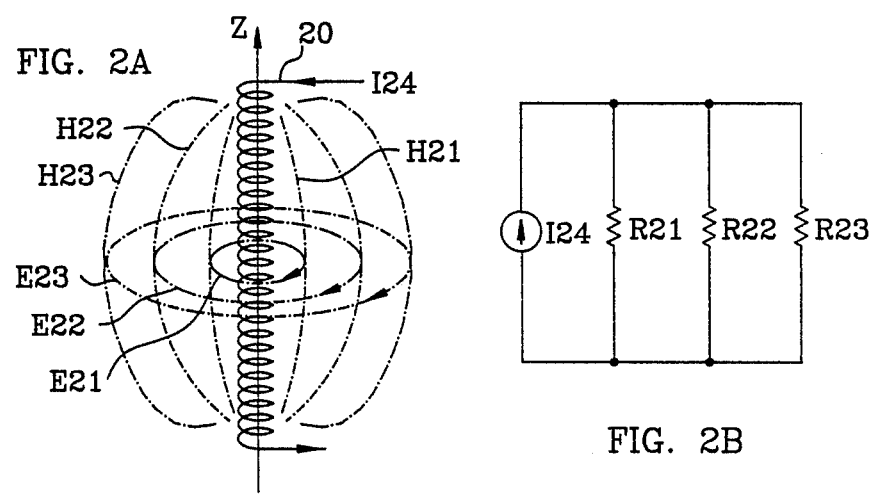
FIG. 2A
FIG. 2B

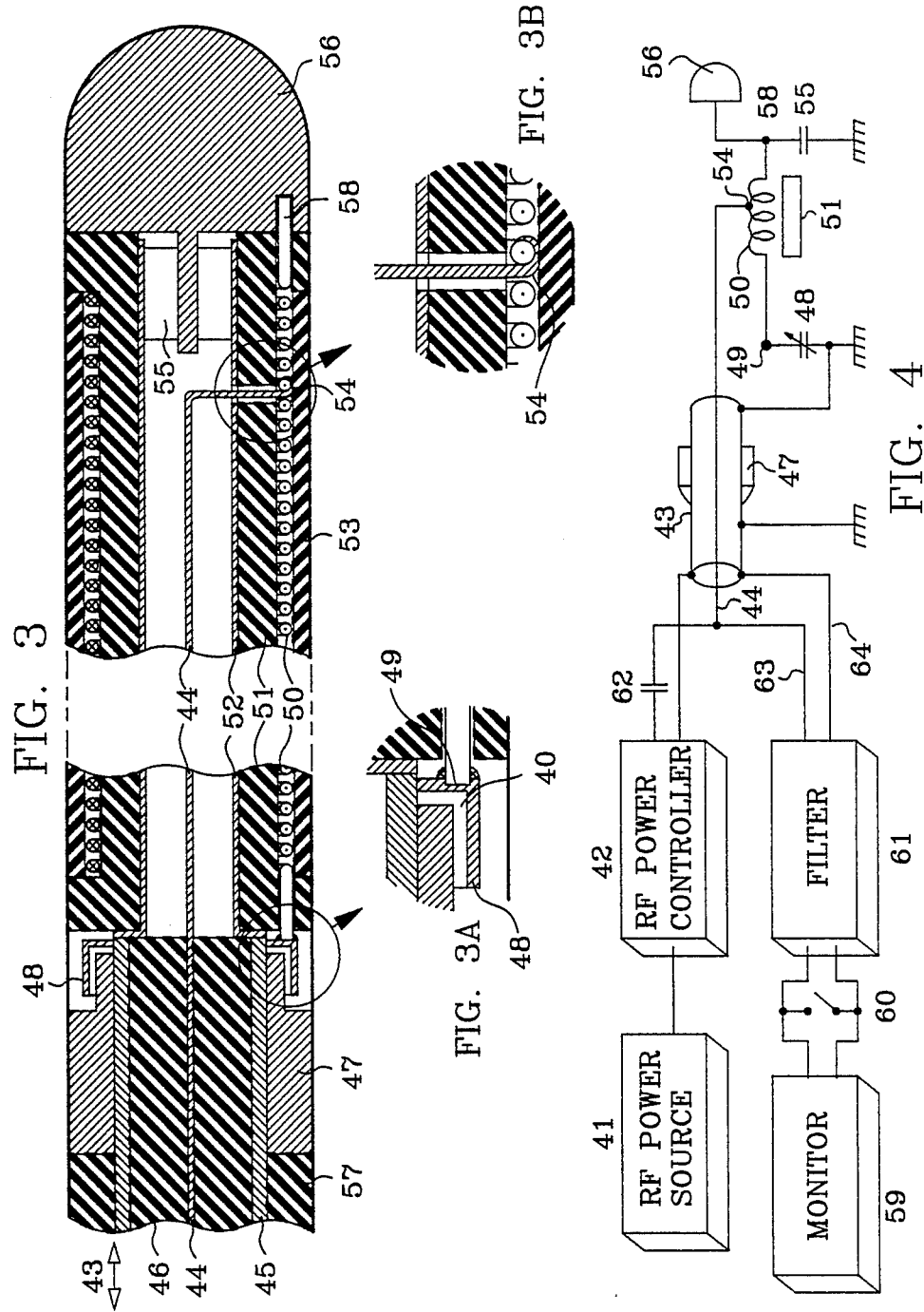

CATHETER WITH RADIOFREQUENCY HEATING APPLICATOR

BACKGROUND OF THE INVENTION

This invention pertains to a catheter designed to couple radiofrequency (RF) energy to biological tissue surrounding the catheter tip. Typical application is in thermal ablation of cardiac tissue.

Percutaneous ablation is a therapeutic procedure used with increasing frequency for treatment of ventricular tachycardia. It works by destroying cardiac tissue responsible for the disease. For example, this subject is covered in *Ablation in Cardiac Arrhythmias*, G. Fontaine & M. M. Scheinman (Eds.), Futura Publishing Company, New York, 1987. A recent review of this field is given in a chapter by D. Newman, G. T. Evans, Jr., and M. M. Scheinman entitled "Catheter Ablation of Cardiac Arrhythmias" in the 1989 issue of *Current Problems in Cardiology*, Year Book Medical Publishers.

Currently, catheter ablation is performed by delivering a high voltage direct current pulse from a standard defibrillator through an electrode catheter designed for temporary pacing. Radiofrequency (RF) ablation using electrosurgical power units is in clinical investigation, as a safer ablation alternative to high voltage direct current pulses. Continuous, unmodulated RF output in the frequency range of 500 KHz to 1.2 MHz is typically used. (RF without qualifiers refers to the electromagnetic spectrum from 10 kHz to 100 GHz.) Laser energy is also being tested for catheter ablation of arrhythmias.

Some experimentation has been reported with the use of microwave energy for catheter ablation. U.S. Pat. No. 4,641,649 issued Feb. 10, 1987 to P. Walinski, A. Rosen and A. Greenspon describes a catheter consisting of a miniature coaxial line terminated in a protruding inner conductor antenna. This system operates at 925 MHz. Another microwave ablation catheter experiment has been reported by K. J. Beckman, & J. C. Lin et al, "Production of Reversible Atrio-Ventricular Block by Microwave Energy" abstracted in *Circulation* 76 (IV): IV-405, 1987. Technical details of a folded dipole applicator catheter used by Beckman have been described by J. C. Lin and Yu-jin Wang in "An Implantable Microwave Antenna for Interstitial Hyperthermia" in *Proceedings of the IEEE*, Vol. 75 (8), p. 1132, August, 1987. An earlier microwave applicator which fits into a blunt-ended mylar catheter has been described by B. E. Lyons, R. H. Britt, and J. W. Strohbehn in "Localized Hyperthermia in the Treatment of Malignant Brain Tumors Using an Interstitial Microwave Antenna Array", *IEEE Trans on Biomedical Engineering*, Vol. BME-31 (1), pp. 53–62, January, 1984.

A general geometrical requirement of catheter-based applicators is that they must be confined in slender cylindrical structure with a radius commensurate with the catheter diameter. In the discussion of catheter applicators which follows, it is convenient to adopt a cylindrical coordinate system with the z-axis coincident with the catheter axis and pointed toward the distal end. The radial component is at the direction normal to the z-axis and the circumferential component has a direction around the z-axis. Radius "r" is measured from the catheter axis. The catheter diameter is "a".

A common feature of all of the above RF catheters (the laser catheter which is an optical device will not be discussed further) is that the energy delivery is predominantly via an electric field (E-field) originating at the applicator's electrode/tissue interface. This class of catheter applicator will therefore be referred to as E-field applicators. Although the configurations of the E-field applicators described above vary, the E-field coupling causes a rapid decrease in current density and therefore tissue heating, as a function of distance from the electrode.

In order to represent the state of the art of RF heating catheters and to compare it with the preferred embodiment of this invention, a simplified E-field applicator is shown in FIG. 1A. Applicator electrode 10 is a wire immersed in a lossy dielectric medium which has electrical properties typical of muscle tissue. In spite of the simple geometry and low frequency approximation used in the description, FIG. 1 retains the salient feature of an E-field coupling.

In FIG. 1A, RF potential V14 is applied between applicator electrode 10 and a remote boundary 15 which corresponds to a neutral electrode applied to the skin. The exact location of boundary 15 is not important to the shape of the E-field near applicator electrode 10. Radial electric field E16 coincides with current density vector $J_r = \sigma E_r$ in the tissue, where $\sigma$ is the conductivity of the tissue.

Continuity of current in a cylindrical geometry in FIG. 1 results in current density which decreases with the inverse square of the radius r. Therefore, corresponding electrical power dissipation resulting in heating of tissue decreases with the fourth power of $a/r$. Typically, an electrode radius is limited by practical catheter size to a maximum of 1 mm. In order to effectively ablate ventricular tachycardia (see Moran, J. M., Kehoe, R. F., Loeb, J. M., Lictenthal, P. R., Sanders, J. H. & Michaelis, L. L. "Extended endocardial Resection for the Treatment of Ventricular Tachycardia and Ventricular Fibrillation", *Ann Thorac Surg* 1982, 34: 538–43), it is desirable to heat tissue up to 10 mm from the catheter axis. In the applicator represented by electrode 10 in FIG. 1A, heat dissipation at the catheter surface is 10,000 times more intense than heat dissipation at a 10 mm radius.

In order to examine the effect of this wide range of heat dissipation, it is useful to divide the lossy medium in FIG. 1A into three cylindrical shells: first shell R11 adjacent to the applicator electrode 10, followed by shell R12, and R13 beginning at the 10 mm radius. Since the shells are traversed by the same current and the potential drop across the shells is additive, energy delivery can be represented by three resistances R11, R12, and R13 in FIG. 1B, connected in series with the source of RF potential V14.

A very steep heating gradient at the applicator electrode 10 tends to desiccate blood or tissue close to the electrode, increasing the resistivity of R11. This in turn further increases the relative power dissipation in R11 in comparison with R12 and R13, until effective impedance of the desiccated region R11 becomes, in effect, an open circuit shutting off the flow of RF power to the tissue beyond R11. This indeed is the problem of state-of-the-art RF ablation catheters which severely limits effective heat delivery to more distant tissue.

Insulation of the applicator electrode 10 from the tissue does not reduce the heat dissipation gradient: If the applicator electrode 10 is insulated from the lossy medium by a thin dielectric tube, the effect of the dielectric can be represented by capacitor (not shown) in series with the source of RF potential V14. Now the applicator must be operated at a frequency high enough so that the impedance of the sum of resistances R11 and R12 and R13 must be higher than the capacitive impedance of the dielectric tube. R11 still dominates the heat distribution.

Therefore in biomedical applications, there is a need for a catheter-compatible RF energy delivery system which dissipates heat more uniformly to a specified depth, thereby leading to a more accurately controlled and larger ablated region. It is also desirable to eliminate the effect of desiccation of tissue adjacent to the electrode on heat dissipation to surrounding tissue.

OBJECT OF THE INVENTION

Accordingly, the principal object of the invention is an RF energy applicator which is housed in a biomedical catheter, typically of 2 mm diameter. This applicator exhibits deeper and more uniform heat dissipation and is not subject to power reduction from desiccation of tissue in the proximity of the applicator, typical of state-of-the-art devices.

A further object of the invention is a cardiac ablation system which provides monitoring and control of RF power fed to the catheter and which also provides signal processing, monitoring and display of the intracardiac electrogram. In this application, the RF energy applicator is configured to allow recording of intracardiac electrograms in proximity to the catheter tip. This is important in order to accurately localize the cardiac tissue to be ablated.

A still further object of the invention is a localized hyperthermia system for cancer treatment, where the catheter with RF energy applicator offers adjustable depth of heating compatible with a tumor size. This system also provides monitoring and control of RF power fed to the catheter for proper thermal dosimetry.

Further advantages of the invention will become apparent from the consideration of the drawings and the ensuing description thereof.

BRIEF DESCRIPTION OF THE DRAWINGS

FIG. 1A shows the electric field (E-field) applicator represented by a conductor immersed in a lossy dielectric medium (state of the art).

FIG. 1B is an equivalent circuit of heat delivery of an E-field applicator (state of the art).

FIG. 2A shows a solenoidal applicator in the form of a helix immersed in a lossy dielectric medium.

FIG. 2B is an equivalent circuit of heat delivery of a solenoidal applicator.

FIG. 3 shows details of a catheter tip mounted solenoidal applicator with intracardiac electrogram monitoring capability.

FIG. 3A and FIG. 3B show magnified details of the circled portions of FIG. 3.

FIG. 4 is a block diagram of RF heating and intracardiac electrogram monitoring ablation catheter system.

DETAILED DESCRIPTION OF THE PREFERRED EMBODIMENT

FIGS. 1A and 1B, which illustrate the problems inherent to state-of-the-art E-field applicators, have already been discussed in the Background section above.

FIG. 2 shows a conductor in the form of a helix 20 traversed by RF current I24. A helix radius in a catheter application is typically $a=1$ mm and maximum desired radius of tissue heating for cardiac ablation is $R=10$ mm. The resultant magnetic field typified by $H_{21}$, $H_{22}$ and $H_{23}$ has primarily an axial (z) component and induces a transverse electric field $E_\phi$ typified by $E_{21}$, $E_{22}$, and $E_{23}$ (and a proportional current density not shown), primarily in the circumferential direction around the helix. The circumference of $E_{22}$ corresponds to R.

At an operating frequency of 915 MHz, and within a cylinder of a radius of 10 mm, the magnitude of induced electric field $E_\phi$ (and corresponding current density $J = \sigma E_\phi$) decreases approximately as $a/r$, where a is the radius of the helix. The z component of electric field $E_z$, which follows field lines similar to $H_{21}$, $H_{22}$ and $H_{23}$, decreases with radius r even more slowly than $a/r$. Hence the heating power dissipation decreases no faster than $(a/r)^2$. For a typical catheter radius $a=1$ mm and desirable depth of heat penetration in ablation $R=10$ mm, the ratio of heat dissipation at the catheter wall to heat dissipation at $R=10$ mm is approximately 100:1. It should be noted that this is a major improvement over the ratio of heat dissipation for the E-field applicator which for the same conditions is 10,000:1.

With a solenoidal applicator, the effective heat dissipation radius R can be adjusted: R increases with decreasing frequency. For ablation of cardiac arrhythmias, ISM (industrial, scientific, and medical) frequencies of 915 MHz and 2450 MHz are of interest. For hyperthermia treatment of cancer, a wider gamut of frequencies is needed depending on the size of a tumor.

FIG. 2B shows an equivalent circuit of a helical heating applicator. Within a volume inside a radius of 10 mm, a circular induced electric field $E_{100}$ multiplied by the length of its circumference gives a potential around each cylindrical shell which is approximately equal. The shell of lossy medium adjacent to the helix, energized by $E_{21}$, the shell at the intermediate distance energized by $E_{22}$, and the shell corresponding to $R=10$ mm energized by $E_{22}$, appear in FIG. 2B as parallel resistances R21, R22, and R23 respectively, exposed to the same potential. Current source I24 feeds the three resistances.

Now, if desiccation occurs adjacent to the helix, resistance R21 increases. This reduces power dissipation in R21 and increases power dissipation in resistances R22 and R23. In general then, as power is increased to a point of desiccation at a catheter surface, the heat delivered to a desiccated volume decreases in a solenoidal applicator while it increases in an E-field applicator. Thus, the solenoidal applicator is much less likely to cause excessive desiccation but even if desiccation occurs, it will not lead to a decrease in power dissipation in remote tissue at $R=10$ mm.

The helix in FIG. 2A is an example of a solenoidal applicator structure, characterized in general by current loop or loops and an electrical short as an end termination. Solenoidal applicator generates a magnetic field in the surrounding tissue. This magnetic field by induction generates in turn, an electric field and current which heats the tissue. In contrast, the E-field applicator has an electrical open end termination and the primary, rather than induced, electric field heats the tissue.

The preferred embodiment of the helical solenoidal applicator in an ablation catheter is shown in FIG. 3. Coaxial line 43 consists of a center conductor 44 (0.16 mm diameter), a dielectric 46 (1.35 mm outside diameter), a metal braid 45 and insulating sleeve 57 (1.8 mm outside diameter). Small diameter and flexible construction makes the coaxial line 43 suitable for a biomedical catheter application. Helical winding 50 is wound on a ceramic or ferrite core 51. A heat-shrunk TEFLON(TFE: Tetrafluoroethylene sleeve 53 covers the helical winding 50.

Distal end of the helical winding 50 is connected at distal peripheral terminal 58 to distal electrode 56 and to bypass capacitor 55. Bypass capacitor 55 is connected to braid 45 through metallized coating 52 on the inside of core 51. The function of the bypass capacitor 55 is to ground the RF energy. Thus during RF current flow through helical winding 50, distal electrode 56 has no RF voltage thereby preventing E-field heating. Distal electrode 56 in conjunction with a proximal ring electrode 47 picks up a cardiac electrogram voltage between them. The distance from the beginning of proximal ring electrode 47 to the end of the distal electrode 56 is 20 mm.

A number of turns on the helical winding 50 is chosen so that at an operating frequency of 915 MHz, the helix is somewhat short of being a quarter wavelength resonator. The proximal end of the helical winding 50 is connected to a variable tuning capacitor 48 at proximal peripheral terminal 49. Variable tuning capacitor 48 is moved with respect to neutral electrode 47 during manufacture for tuning to a precise quarter wavelength resonance. Details of the tuning capacitor 48 are shown magnified in FIG. 3A.

RF power is coupled into the helical resonator by connecting the center conductor 44 to the helical winding 50 at feed terminal 54. The connection at feed terminal 54 is shown magnified in FIG. 3B. The position of feed terminal 54 on the helix is selected for good match between the characteristic impedance of the line and the impedance of the resonator.

The choice of an axial quarter wavelength resonator is by no means unique. One could just as well select any multiplicity of quarter wavelengths e.g., half wavelength or full wavelength resonators.

In some applications, it may be desirable to distort the axisymetrical form of the induced E-field. This can be accomplished by partially covering a dielectric sleeve 53 with metal foil (not shown). Currents induced in such foil modify the shape of a heating pattern and so serve as an aperture antenna. An asymmetrical field pattern can also be accomplished by a loop antenna.

In cardiac ablation, it is highly desirable to be able to monitor intracardiac electrogram just before and after the application of heat. FIG. 4 shows a block diagram of a system which combines dosimetry control of the solenoidal heat delivery with monitoring of intracardiac electrograms.

The RF power is generated in an RF power source 41. The RF power is controlled and monitored in controller 42 which couples the RF power to the coaxial line 43 through capacitor 62, which for RF represents substantially a short-circuit.

The center conductor 44 is attached at feed terminal 54 to the helical winding 50 wound on a core 51. Quarter wavelength resonance tuning is accomplished by adjustment of variable tuning capacitor 48 connected to the helical winding 50 at proximal peripheral terminal 49. The RF ground is maintained by the bypass capacitor 55 connected to the distal electrode 56 and then to helical winding 50 at distal peripheral terminal 58.

Distal electrode 56 in conjunction with the proximal ring electrode 47 picks up the local intracardiac electrograms and feeds this electrogram signal through the coaxial line 43 to capacitor 62. Capacitor 62 represents a short circuit for the RF power and an open circuit for the much lower frequency band (typically 0.1 Hz to 100 Hz) associated with intracardiac electrogram activity. The electrogram signal appears therefore on lines 63 and 64 at the input to the low-pass filter 61.

Filter 61 has a high input impedance to the RF and hence has no effect on transmission of RF power between controller 42 and coaxial line 43. Filter 61 blocks the transmission of the RF power to switch 60 while allowing passage of the electrogram signal. Switch 60 is closed simultaneously with application of RF power, thus providing additional protection for monitor 59. Electrogram signal processing, display, and recording is accomplished by monitor 59. Standard existing equipment is suitable for application as monitor 59.

Solenoidal catheter applicator for hyperthermia treatment of tumors follows largely the same design as the one represented in FIG. 3 except that in this case, there is no need for the distal electrode 56 and the proximal ring electrode 47. Since the depth of heat penetration depends inversely on the square root of frequency, the frequency of operation and the helical winding design can be tailored to the required depth of penetration depending on tumor size.

While certain specific embodiments of improved RF heating applicator and systems have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A radiofrequency (RF) heating and monitoring applicator connected to an RF energy source and an intracardiac electrogram monitor, and comprising
    a transmission line having a proximal end connected to the RF energy source and to said monitor and further having a distal end;
    a solenoidal antenna at said distal end of said transmission line commensurate with the transmission line in diameter;
    at least one monitoring electrode carried on said antenna; and
    coupling means for connection of said solenoidal antenna to said monitoring electrode and to the transmission line for providing efficient coupling of RF energy from the RF energy source through the transmission line to the solenoidal antenna and for transmitting lower frequency intracardiac potential intercepted by said at least one monitoring electrode to said proximal end of the transmission line.

2. An RF heating and monitoring applicator in accordance with claim 1, wherein: said source of RF energy is adapted for generating a frequency for which a skin depth of lossy medium adjacent to the applicator is equal to a desired depth of heat penetration.

3. An RF heating and monitoring applicator in accordance with claim 1, wherein: said transmission line is a flexible coaxial line with a diameter of an order of a few millimeters and a length of an order of meters suitable for use as a catheter.

4. An RF heating and monitoring applicator in accordance with claim 1, wherein:
    said transmission line further comprises a first conductor and a second conductor;
    the solenoidal antenna comprises a conductor helix with a feed terminal and at least one peripheral terminal;

said at least one electrode comprises a distal monitoring electrode and a proximal monitoring electrode for providing contact surfaces to the outside of the applicator; and the coupling means comprises a connection between the first conductor and the feed terminal, at least one capacitive coupling between the second conductor and the at least one peripheral terminal, a connection between the distal monitoring electrode and the helix, and a connection between the proximal monitoring electrode and the second conductor.

5. An RF heating and monitoring applicator in accordance with claim 4, wherein the capacitive coupling includes a space between the second conductor and said at least one peripheral terminal.

6. An RF heating and monitoring applicator in accordance with claim 4, wherein:

said at least one peripheral terminal comprises a first peripheral terminal and a second peripheral terminal;

said at least one capacitive coupling between the second conductor and the at least one peripheral terminal comprises a first capacitive coupling between said second conductor and said first peripheral terminal for tuning, and further comprises a second capacitive coupling between said second conductor and said second peripheral terminal for bypass of RF energy; and said distal monitoring electrode is connected to the helix at the second peripheral terminal.

7. An RF heating and monitoring applicator in accordance with claim 1, wherein: said solenoidal antenna is wound on a ferrite core to increase efficiency of generation of an external magnetic field.

8. An RF heating and monitoring applicator in accordance with claim 1, wherein: said solenoidal antenna comprises a conductor loop tuned and coupled to the transmission line for assuring efficient flow of energy from said source of RF energy to a lossy medium on the outside of the applicator.

9. An RF heating and monitoring applicator in accordance with claim 1, wherein: said solenoidal antenna is partially covered by a shield to control generation of an external electromagnetic field and a pickup of an intracardiac electrogram signal.

10. An RF heating and monitoring cardiac ablation catheter system comprising source and controller of RF energy;

an intracardiac electrogram monitor;

a thin and flexible catheter transmission line having a proximal end and a distal end;

a proximal coupling means for interconnection of said source and controller of RF energy and said intracardiac electrogram monitor to the proximal end of said catheter transmission line;

a solenoidal antenna connected to the distal end of the catheter transmission line;

at least one intracardiac electrogram pickup electrode at the distal end of the catheter transmission line; and a distal coupling means for connection of said solenoidal antenna and said at least one intracardiac electrogram pickup electrode to a distal end of said catheter transmission line, said proximal and distal coupling means with said transmission line further comprising frequency-sensitive filter elements, for transmitting RF power from the source to the solenoidal antenna and for transmitting an intracardiac electrogram signal from said at least one intracardiac electrogram pickup electrode to the monitor.

* * * * *